United States Patent [19]
Desai et al.

[11] Patent Number: 5,973,180
[45] Date of Patent: Oct. 26, 1999

[54] PROCESS FOR THE PRODUCTION OF AN N-ACYL DERIVATIVE OF O,S-DIALKYL PHOSPHOROAMIDOTHIOATE

[75] Inventors: Vijay C. Desai, Shawnee, Kans.; David T. Erdman, Koln, Germany; Klaus Jelich, Overland Park; Peter E. Newallis, Leawood, both of Kans.

[73] Assignee: Bayer Corporation, Pittsburgh, Pa.

[21] Appl. No.: 09/143,769

[22] Filed: Aug. 31, 1998

[51] Int. Cl.$^6$ .................................................. C07F 9/24
[52] U.S. Cl. ........................................... 558/144; 558/178
[58] Field of Search ..................................... 558/144, 178

[56] References Cited

U.S. PATENT DOCUMENTS 3,716,600  2/1973  Magee .
3,732,344  5/1973  Platt, Jr. .

Primary Examiner—Michael G. Ambrose
Attorney, Agent, or Firm—Joseph C. Gil; Carol Marmo

[57] ABSTRACT

The present invention relates to an improved process for the preparation of an acyl derivative of O,S-dialkyl phosphoroamidothioate by reacting an O,S-dialkyl phosphoroamidothioate with an acylating agent in the presence of an acid, wherein the improvement resides in adding a $C_4$ to $C_8$ aliphatic alcohol, following completion of the acylation reaction, to the mixture of the N-acyl-O,S-dialkyl phosphoroamidothioate, the acylating agent and the acid. In an embodiment of the present invention, the acylation reaction is conducted in the absence of a solvent. The aliphatic alcohol is easily recovered and can be reused in a subsequent acylation reaction.

23 Claims, No Drawings

PROCESS FOR THE PRODUCTION OF AN N-ACYL DERIVATIVE OF O,S-DIALKYL PHOSPHOROAMIDOTHIOATE

TECHNICAL FIELD OF THE INVENTION

The field of the present invention is the preparation of an acyl derivative of O,S-dialkyl phosphoroamidothioate. More particularly, the present invention pertains to an improved process for the preparation of the acyl derivative of O,S-dimethyl phosphoroamidothioate known as Orthene. Orthene is produced by reacting an O,S-dialkyl phosphoroamidothioate with an acylating agent in the presence of an acid, wherein the improvement comprises the addition of a $C_4$ to $C_8$ aliphatic alcohol, following completion of the acylation reaction, to isolate and recover the Orthene.

BACKGROUND OF THE INVENTION

The acyl derivative of O,S-dimethyl phosphoroamidothioate is known as Orthene. Orthene is typically produced by reacting O,S-dimethyl phosphoroamidothioate with conventional acylating agents such as acid anhydrides. Acetic acid anhydride is a preferred acylating agent. The acylation reaction is typically carried out at temperatures of from 0° C. to 60° C. in the presence of a catalytic amount of an acid, and in the presence of a solvent. Such solvents include methylene chloride, chloroform, tetrahydrofuran and benzene (see, e.g., U.S. Pat. Nos. 3,716,600 and 3,732,344).

The solvents utilized in the process are suspected carcinogens. Moreover, tetrahydrofuran tends to form dangerous peroxide upon storage. Thus, methylene chloride, chloroform, tetrahydrofuran and benzene are not commercially viable solvents. It would be desirable to develop a process for producing Orthene which does not require the use of a volatile, toxic solvent.

BRIEF SUMMARY OF THE INVENTION

It is an object of the present invention to provide an improved process for the preparation of an acyl derivative of O,S-dialkyl phosphoroamidothioate comprising reacting an O,S-dialkyl phosphoroamidothioate with an acylating agent in the presence of an acid, wherein the improvement resides in the addition of a $C_4$ to $C_8$ aliphatic alcohol to the reaction mixture following completion of the acylation reaction to isolate and recover the Orthene.

It is also an object of the present invention to provide a process for producing an acyl derivative of O,S-dialkyl phosphoroamidothioate in the absence of a volatile, toxic solvent.

These and other objects that will be apparent to those skilled in the art are accomplished by the addition of a $C_4$ to $C_8$ aliphatic alcohol to the acylating mixture, following completion of the acylation reaction, to isolate and recover the acyl derivative of O,S-dialkyl phosphoroamidothioate.

DETAILED DESCRIPTION OF THE PREFERRED EMBODIMENTS OF THE INVENTION

The present invention is directed to an improved process for the preparation of an acyl derivative of O,S-dialkyl phosphoroamidothioate by reacting an O,S-dialkyl phosphoroamidothioate with an acylating agent in the presence of an acid, wherein the improvement resides in the addition of a $C_4$ to $C_8$ aliphatic alcohol as a solvent to isolate and recover the acyl derivative of O,S-dimethyl phosphoroamidothioate. The $C_4$ to $C_8$ aliphatic alcohol is added to the mixture of the O,S-dialkyl phosphoroamidothioate, the acylating agent and the acid, following completion of the acylation reaction. In an embodiment of the present invention, the acylation reaction is conducted in the absence of a solvent. The aliphatic alcohol is easily recovered and can be reused in a subsequent process to isolate and recover the O,S-dialkyl phosphoroamidothioate.

In a preferred embodiment, the O,S-dialkyl phosphoroamidothioate, the acylating agent, and the acid are added to a reactor and heated for a period of from about 0.5 hour to about 8 hours, preferably from about 1 hour to about 3 hours, at a temperature of from about 20° C. to about 80° C., and preferably from about 40° C. to about 60° C. Any excess acylating agent is stripped off under vacuum. The mixture is cooled to a temperature of from about 0° C. to about 10° C. and neutralized to a pH of from about 7.0 to about 7.2 by the addition of a base. Such bases include ammonium hydroxide, sodium hydroxide, potassium hydroxide, sodium carbonate or potassium carbonate. Water in an amount of from about 10% to about 50% by weight (based on the combined weight of the reactants), and an aliphatic alcohol are added to the mixture following completion of the acylation reaction. The resultant two phases (an organic/alcohol phase and an aqueous phase) are separated and the aqueous phase is extracted with the alcohol. The alcohol phases are combined and concentrated, the mixture is cooled to a temperature of from about 0° C. to about 10° C., and filtered to recover the desired acyl derivative. The filtrate is distilled to recover the aliphatic alcohol.

The O,S-dialkyl phosphoroamidothioates as well as the methods of manufacture thereof are known in the art, and are described in U.S. Pat. No. 3,309,266, the disclosure of which is herein incorporated by reference. Such O,S-dialkyl phosphoroamidothioates include O-methyl-S-methyl phosphoroamidothioate, O-methyl-S-ethyl phosphoroamidothioate, O-ethyl-S-methyl phosphoroamidothioate, O-methyl-S-ethyl phosphoroamidothioate, O-ethyl-S-propyl phosphoroamidothioate and the like. A preferred O,S-dialkyl phosphoroamidothioate is O-methyl-S-methyl phosphoroamidothioate.

Acylating agents are also known in the art, and include acyl halides, ketenes and acid anhydrides. Preferred acylating agents are acetic acid anhydride and acetyl chloride.

Acid catalysts are known and include phosphoric acid, sulfuric acid, methanesulfonic acid, nitric acid, hydrochloric acid, perchloric acid, and acidic ion exchange resins (such as Amberlyst N15). A preferred acid catalyst is sulfuric acid.

The acylation reaction is typically carried out at temperatures of from about 0° C. to about 80° C. Pressure is not critical in the reaction. For convenience, atmospheric pressure is generally used. Under usual conditions, stoichiometric proportions or a slight excess of acylating agent is used. The amount of acid catalyst can vary over a wide range and is typically from about 0.5% to about 50% by weight, and preferably from about 1% to about 3% by weight, based on the combined weight of the O,S-dialkyl phosphoroamidothioate and the acylating agent.

The improved process of the present invention includes the addition of a $C_4$ to $C_8$ aliphatic alcohol, following completion of the acylation reaction, to isolate and recover the acyl derivative of the O,S-dimethyl phosphoroamidothioate. Such aliphatic alcohols include n-butyl alcohol, pentanol and the various isomers thereof; 4-methyl-2-pentanol, t-butanol, isobutyl alcohol, 2-methyl-1-butanol, hexanol and the various isomers thereof; heptanol and the various isomers thereof; and octanol and the various isomers thereof. Preferred alcohols are n-butyl alcohol, n-pentanol and 4-methyl-2-pentanol. The amount of alcohol can vary over a wide range and is typically from about 100% to about 500% by weight, and preferably from about 200% to about 400% by weight, based on the combined weight of the O,S-dialkyl phosphoroamidothioate and the acylating agent.

A preferred embodiment, includes the addition of water to the mixture following completion of the acylation reaction. The amount of water can vary over a wide range and is typically from about 10% to about 50% by weight, based on the combined weight of the O,S-dialkyl phosphoroamidothioate and the acylating agent.

The invention is further illustrated but is not intended to be limited by the following examples in which all parts and percentages are by weight unless otherwise specified.

EXAMPLE

To a mixture of O,S-dimethyl phosphoroamidothioate (1.0 mole, 183.2 g, of 77% purity) and concentrated $H_2SO_4$ (0.05 mole, 5.1 g, of 96% purity), was added acetic anhydride (1.30 mole, 132.6 g) slowly for 45 minutes at 40° C. to 50° C.

The mixture was then cooked from 1 hour to 1.5 hours at a temperature of from 50° C. to 55° C. The resultant acetic acid, thus formed was stripped off along with the excess acetic anhydride at 75° C./10 mm using a rotary evaporator.

The molten mass containing N-acetyl O,S-dimethyl phosphoroamidothioate was mixed with 100 ml of water (fresh or recycled from the previous batch) and 750 ml of 4-methyl-2-pentanol (the aliphatic alcohol). This mixture was then cooled to a temperature of 5° C. and neutralized with a 30% aqueous ammonium hydroxide solution to a pH of from about 6.8 to about 7.2. Controlling the temperature and pH of the mixture was important to prevent hydrolysis of the N-acetyl derivative of O,S-dimethyl phosphoroamidothioate. The aqueous phase was separated and extracted with 2×200 ml of fresh 4-methyl-2-pentanol (the aliphatic alcohol).

The organic (alcohol) phases were combined and concentrated to 400 ml. The concentrated organic phase was cooled to 10° C. and the N-acetyl-O,S-dimethyl phosphoroamidothioate was collected via filtration. The filter cake was washed with cold (5° C. to 10° C.) 4-methyl-2-pentanol twice (50 ml each). The collected Orthene crystals were further purified as follows: The mother liquor and washings were combined and 70% of it was recycled as-is in the next batch while the remaining 30% of it was extracted with 100 ml. of water (this water can be mixed with the molten mass containing N-acetyl O,S-dimethyl phosphoroamidothioate as described above). The organic phase was distilled to recover the 4-methyl-2-pentanol.

The collected Orthene was mixed with 400 ml. of 4-methyl-2-pentanol at 40° C. for 10 minutes, stirred vigorously, cooled to 10° C., filtered, and dried. The Orthene thus obtained was 99% pure. The average yield of Orthene over 10 recycles was 84%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of an N-acyl derivative of an O,S-dialkyl phosphoroamidothioate by reacting an O,S-dialkyl phosphoroamidothioate with an acylating agent in the presence of an acid, wherein the improvement comprises adding a $C_4$ to $C_8$ aliphatic alcohol to the reaction mixture following completion of the acylation reaction, to isolate and recover the N-acyl derivative.

2. The process of claim 1 wherein the acylation reaction is conducted in the absence of a solvent.

3. The process of claim 1 wherein the reaction mixture is heated to a temperature of from about 20° C. to about 80° C.

4. The process of claim 1 wherein the reaction mixture is heated to a temperature of from about 40° C. to about 60° C.

5. The process of claim 1 wherein the O,S-dialkyl phosphoroamidothioate is selected from the group consisting of O-methyl-S-methyl phosphoroamidothioate, O-methyl-S-ethyl phosphoroamidothioate, O-ethyl-S-methyl phosphoroamidothioate, O-methyl-S-ethyl phosphoroamidothioate, or O-ethyl-S-propyl phosphoroamidothioate.

6. The process of claim 1 wherein the O,S-dialkyl phosphoroamidothioate is O-methyl-S-methyl phosphoroamidothioate.

7. The process of claim 1 wherein the acylating agent is selected from the group consisting of an acyl halide, ketene or acid anhydride.

8. The process of claim 7 wherein the acylating agent is acetic acid anhydride or acetyl chloride.

9. The process of claim 1 wherein the acid catalyst is selected from the group consisting of phosphoric acid, sulfuric acid, methanesulfonic acid, nitric acid, hydrochloric acid, perchloric acid, or acidic ion exchange resins.

10. The process of claim 1 wherein the acid catalyst is sulfuric acid.

11. The process of claim 1 wherein the acid catalyst is from about 0.5% to about 50% by weight of the combined weight of the O,S-dialkyl phosphoroamidothioate and the acylating agent.

12. The process of claim 1 wherein the acid catalyst is from about 1% to about 3% by weight of the combined weight of the O,S-dialkyl phosphoroamidothioate and the acylating agent.

13. The process of claim 1 wherein the aliphatic alcohol is selected from the group consisting of n-butyl alcohol, pentanol or the various isomers thereof; 4-methyl-2-pentanol, t-butanol, isobutyl alcohol, 2-methyl-1-butanol, hexanol or the various isomers thereof; heptanol or the various isomers thereof; or octanol or the various isomers thereof.

14. The process of claim 1 wherein the aliphatic alcohol is selected from the group consisting of n-butyl alcohol, n-pentanol or 4-methyl-2-pentanol.

15. The process of claim 1 wherein the amount of alcohol is from about 100% to about 500% by weight of the combined weight of the O,S-dialkyl phosphoroamidothioate and the acylating agent.

16. The process of claim 1 wherein the amount of alcohol is from about 200% to about 400% by weight of the combined weight of the O,S-dialkyl phosphoroamidothioate and the acylating agent.

17. The process of claim 1 wherein water is added to the reaction mixture following completion of the acylating reaction.

18. The process of claim 17 wherein the amount of water is from about 10% to about 50% by weight of the combined weight of the O,S-dialkyl phosphoroamidothioate and the acylating agent.

19. The process of claim 1 wherein a base is added to the reaction mixture to neutralize the mixture to a pH of from about 7.0 to about 7.2.

20. The process of claim 19 wherein the base is selected from the group consisting of ammonium hydroxide, sodium hydroxide, potassium hydroxide, sodium carbonate, or potassium carbonate.

21. The process of claim 1 wherein resultant organic phases of the acylation reaction are separated and an aqueous phase is extracted with the aliphatic alcohol, resultant alcohol phases are combined, the mixture is cooled to a temperature of from about 0° C. to about 10° C. and filtered to recover the desired N-acyl derivative, the filtrate is then distilled to recover the aliphatic alcohol.

22. The process of claim 21 wherein the aliphatic alcohol used for the extraction is selected from the group consisting of n-butyl alcohol, pentanol or the various isomers thereof; 4-methyl-2-pentanol, t-butanol, isobutyl alcohol, 2-methyl-1-butanol, hexanol or the various isomers thereof; heptanol or the various isomers thereof; or octanol or the various isomers thereof.

23. The process of claim 21 wherein the aliphatic alcohol used for the extraction is selected from the group consisting of n-butyl alcohol, n-pentanol or 4-methyl-2-pentanol.

* * * * *